United States Patent
Oron

(10) Patent No.: US 6,537,304 B1
(45) Date of Patent: Mar. 25, 2003

(54) ISCHEMIA LASER TREATMENT

(76) Inventor: Amir Oron, Davis Pais Street 11, Rishon le Zion (IL), 75260

(*) Notice: Subject to any disclaimer, the term of this patent is extended or adjusted under 35 U.S.C. 154(b) by 0 days.

(21) Appl. No.: 09/701,838
(22) PCT Filed: May 31, 1999
(86) PCT No.: PCT/IL99/00287

§ 371 (c)(1),
(2), (4) Date: Apr. 12, 2001

(87) PCT Pub. No.: WO99/62599

PCT Pub. Date: Dec. 9, 1999

(30) Foreign Application Priority Data

Jun. 2, 1998 (IL) .................................. 124722

(51) Int. Cl.$^7$ ............................................. A61N 5/067
(52) U.S. Cl. .............................. 607/89; 606/13; 606/16
(58) Field of Search ............................. 607/89, 91, 93; 606/13, 16, 17

(56) References Cited

U.S. PATENT DOCUMENTS

| | | | | |
|---|---|---|---|---|
| 4,966,144 A | | 10/1990 | Rochkind et al. ............ 128/395 |
| 5,358,503 A | * | 10/1994 | Bertwell et al. ................ 606/2 |
| 5,445,146 A | * | 8/1995 | Bellinger ....................... 606/3 |
| 5,580,550 A | | 12/1996 | Gough et al. ............ 424/70.11 |
| 5,580,555 A | | 12/1996 | Schwartz ................... 424/85.1 |
| 5,616,140 A | | 4/1997 | Prescott ....................... 606/10 |
| 5,640,978 A | * | 6/1997 | Wong .......................... 128/898 |
| 6,156,028 A | * | 12/2000 | Prescott ........................... 36/1 |
| 6,358,272 B1 | * | 3/2002 | Wilden ......................... 606/13 |

FOREIGN PATENT DOCUMENTS

| | | |
|---|---|---|
| DE | 295 15096 | 1/1996 |
| EP | 0 130 950 | 1/1985 |
| WO | WO 96/36396 | 11/1996 |

OTHER PUBLICATIONS

Kliegman, et al., "The Fetus and the Neonatal Infant", Part XI, *Nelson's Textbook of Pediatrics*, 15$^{th}$ Edition, W.B. Saunders Company, pp. 431–433, 1996.

Bibikova, A. et al., "Enhancement of Angiogenesis in Regenerating Gastrocnemius Muscle of the Toad (*Bufo viridis*) by Low–Energy Laser Irradiation", *Anatomy and Embryology* (1994), vol. 190, pp. 597–602.

Weiss, N. et al., "Enhancement of Muscle Regeneration in the Rat Gastrocnemius Muscle by Low Energy Laser Irradiation", *Anat. Embryol.* (1992), vol. 186, pp. 497–503.

Bibikova, A. et al., "Promotion of Muscle Regeneration in the Toad (*Bufo viridis*) Gastrocnemius Muscle by Low–Energy Laser Irradiation", *The Anatomical Record*, vol. 235, 1993, pp. 374–380.

Nissan, M. et al., "HeNe Laser Irradiation Delivered Transcutaneously: Its Effect on the Sciatic Nerve of Rats", *Lasers in Surgery and Medicine*, vol. 6, pp. 435–438, 1986.

Assia, E. et al., "Temporal Parameters of Low Energy Laser Irradiation for Optimal Delay of Post–Traumatic Degeneration of Rat Optic Nerve", *Brain Research*, vol. 476, 1989, pp. 205–212.

Conlan, M.J. et al., "Biostimulation of Wound Healing by Low–Energy Laser Irradiation", *Journal of Clin. Periodontology*, vol. 23, 1996, pp. 492–496.

Belkin, M. et al., "A Critical Review of Low Energy Laser Bioeffects", *Lasers and Light in Ophthalmology*, vol. 2, No. 1, pp. 63–71, 1988.

Fisher, M., "Characterizing the Target of Acute Stroke Therapy", *Stroke*, 1997, vol. 28, pp. 866–872.

* cited by examiner

Primary Examiner—Roy D. Gibson
(74) Attorney, Agent, or Firm—Darby & Darby

(57) ABSTRACT

Apparatus (10) for treatment of an ischemic region of brain cells in a cranium, comprising a skull covering (14) adapted to cover at least part of the cranium, at least one guide (16) attached to the skull covering (14), and a laser source (12) which is operative to direct a laser beam through the at least one guide (16) into the cranium. The at least one guide may include an optic fiber or a waveguide.

12 Claims, 2 Drawing Sheets

ISCHEMIA LASER TREATMENT

FIELD OF INVENTION

Cytoprotective effect and increase of survival of neurons in the Central Nervous System (CNS) of mammals following ischemia (as in stroke), by low energy laser (LEL) irradiation.

BACKGROUND OF THE INVENTION

Mammalian CNS neurons have a negligible capacity to regenerate following lesion or acute ischemic (no oxygen supply) conditions. A dramatic decrease or complete abolishment of oxygen supply to the nerve cells and other cells in a certain region of the brain can occur due to occlusion of one or more of the arteries that supply blood to the brain (Fisher M, "Characterizing the Target of Acute Stroke Therapy", Stroke, Vol. 28 No 4 pp. 866–872, April 1997). Concomitantly with this event, the neurons of the brain go through a gradual degeneration process that eventually leads to necrosis in the acute ischemic zone. Clinical syndromes such as paraplegia, quadriplegia, etc., are evident due to dysfunction of the nerve cells in the brain.

The mammalian CNS also has a negligible capacity to regenerate following injury. Limited regeneration of peripheral axons in mammals and CNS in lower vertebrate can take place in a post trauma setting.

Low energy laser irradiation has recently been found to modulate various processes in different biological systems, (Belkin, et al, A critical review of low energy laser bioeffects. Lasers Light Ophthalmology vol. 2 p. 63–71, 1988 and Conlan et al, Biostimulation of wound healing by low energy laser irradiation, Journal of Clinical Periodontology vol. 23, p. 492–496, 1996). The effect of low energy laser irradiation following trauma has been investigated so far in skin, peripheral nerves and skeletal muscles.

Assia et al (Temporal parameters of low energy laser irradiation for optimal delay of post traumatic degeneration of lto rat optic nerve, Brain Research 476: 205–212, 1989) described the possibility of delaying the post traumatic process of degeneration and scar tissue formation of a crushed optic nerve (peripheral nervous system) by low energy laser irradiation.

U.S. Pat. No. 5,580,555 to Schwartz involves the administration of tumor necrosis factor (TNF) to the sight of injury in the optic nerve in order to facilitate regeneration of axons across the sight of the injury. The use of low energy laser in conjunction with the use of the TNF is suggested to augment the effect of TNF. However, Schwartz presents no experimental results to favor the beneficial effect of the laser. Furthermore, it is described in the detailed description that treatment with TNF alone (without laser irradiation) gives good results.

It has previously been suggested that regeneration of injured peripheral nerves can-be accelerated by LEL (Rochkind S. Stimulation effect of laser energy on the regeneration of traumatically injured peripheral nerves. The Krim National Medical Inst., Morphogenesis and Regenerations Vol. 73: pp. 48–50, 1978). Nissan M., Rochkind S. et al (HeNe laser irradiation delivered transcutaneously: its effect on sciatic nerve of rats. Laser. Surg. Med. Vol. 6: pp. 435–438, 1986) also demonstrated that transcutaneous LEL of sciatic nerve induced an increase in the amplitude of the electrical signals recorded in the irradiated nerve, i.e. increased the size of the action potential.

U.S. Pat. No. 4,966,144 to Rochkind et aL. deals with a method of inducing functional regeneration of nerve fibers of an injured sight of the spinal cord (or using grafts of peripheral nerves which were placed into the injured sight) by a light source which generates light at a wavelength of 330–1200 nm. The method involves only the spinal cord but not the brain. Moreover, the method is not related to an acute ischemic phase of nerve cells in the CNS as in a situation of "stroke"nor is the cytoprotective effect of laser irradiation cited in Rochkind et aL It has previously been reported that the low energy laser irradiation causes a decrease in the inflammatory response following injury to skeletal muscles (Bibikova A. & U. Oron. Promotion of muscle regeneration following cold injury to the toad (Bufo Viridis) gastrocnemius muscle by low energy laser irradiation. Anat. Rec. (1993) vol. 235 pp. 374–380 and N. Weiss & Oron Enhancement of muscle regeneration in the rat gastrocnemius muscle by low energy laser irradiation. Anat. Embryol. (1992) Vol. 186 pp. 497–503). The above phenomenon may suggest possible cytoprotective effect of at least the mitochondria and maybe other structures of the cell by the LEL. Thus, LEL irradiation allows cells under stressful conditions of low or no oxygen supply to maintain their viability in spite of the harsh conditions. The irradiated cells most probably do not degenerate to the same extent as the non-irradiated cells and therefore also the inflammatory response, which is typical to tissues undergoing a degenerative process following injury is markedly decreased. Furthermore, LEL irradiation has been found to enhance the process of formation of new blood vessels (angiogenesis) in injured skeletal muscles (Bibikova A, Belkin A. and Oron U. Enhancement of angiogenesis in regenerating gastrocnemius muscle of the toad (Bufo Viridis) by low energy laser irradiation. Anat. Embryol. (1994) Vol. 190 pp. 597–602).

So far, despite significant research efforts for many years worldwide, a safe and effective method of inhibiting or eliminating the adverse irreversible effects of stroke and other ischemic events on brain cells and the significant clinical manifestations of it on animal and human body function has yet to be developed.

SUMMARY OF THE INVENTION

The present invention seeks to provide a novel method and apparatus for using LEL irradiation to protect cells under acute ischemic conditions in the brain. In accordance with the present invention, in the initial phase of ischemia, the LEL irradiation causes an enhanced angiogenesis process which in turn causes a regeneration process in the injured brain cells in the ischemic zone, thereby allowing for greater protection of the cells in the future.

There is thus provided in accordance with a preferred embodiment of the present invention apparatus for treatment of an ischemic region of brain cells in a cranium, including a skull covering adapted to cover at least part of a cranium, at least one guide attached to the skull covering, and a laser source which is operative to direct a laser beam through the at least one guide into a cranium. The at least one guide may include an optic fiber or a waveguide.

In accordance with a preferred embodiment of the present invention the laser source includes a diode laser.

Further in accordance with a preferred embodiment of the present invention a laser controller is operatively connected to the laser source which controls operation of the laser source.

Still further in accordance with a preferred embodiment of the present invention an actuator which is operative to move the laser source further from or closer to a cranium.

Additionally in accordance with a preferred embodiment of the present invention the skull covering includes sealing material at a skull-contacting periphery thereof.

In accordance with a preferred embodiment of the present invention a timer is mounted on the skull covering.

Further in accordance with a preferred embodiment of the present invention an indicator light is mounted on the skull covering.

Still further in accordance with a preferred embodiment of the present invention a plurality of the guides are attached to the skull covering which direct a plurality of the laser beams in a plurality of directions.

Additionally in accordance with a preferred embodiment of the present invention a plurality of the guides are attached to the skull covering which are operative to focus a plurality of the laser beams in a plurality of focal lengths into a cranium.

In accordance with a preferred embodiment of the present invention a plurality of the guides are commonly attached to the laser source.

Further in accordance with a preferred embodiment of the present invention a plurality of the laser sources and a plurality of the guides are provided, wherein each source directs a laser beam through one the guide.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
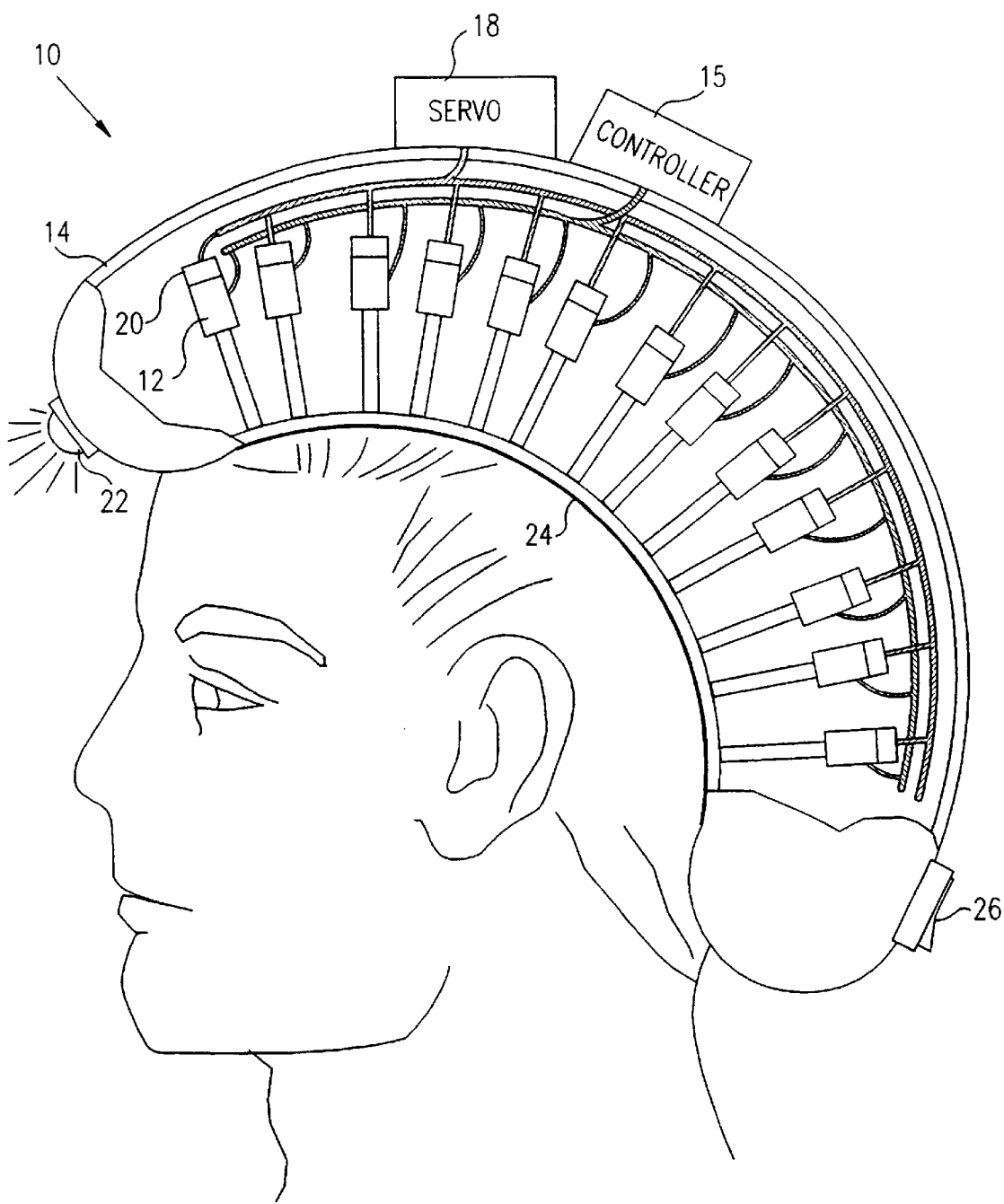
FIG. 1 is a simplified pictorial illustration of apparatus for treatment of an ischemic region of brain cells in a cranium, constructed and operative in accordance with a preferred embodiment of the present invention.

Reference is now made to FIG. 1 which illustrates apparatus 10 for treatment of an ischemic region of brain cells in a cranium, in accordance with a preferred embodiment of the present invention.

Apparatus 10 preferably includes a multiplicity of laser sources 12, such as diode lasers, arranged for multidirectional multifocal irradiation of the cranium. Laser sources 12 are mounted in a skull covering 14, preferably constructed of metal, plastic or any other irradiation blocking material, and are preferably controlled by a laser controller 15, either mounted externally or internally on skull covering 14. Each laser source 12 preferably delivers laser energy to the skull via a guide 16, such as an optic fiber or waveguide. Laser sources 12 are preferably connected to a servo system 18 which includes one or more actuators 20 which can move laser sources further from or closer to the cranium, thereby controlling the distance of the distal ends of guides 16 from the cranium.

Skull covering 14 may cover the entire skull including the brainstem, or alternatively, only part of the skull. Apparatus 10 preferably includes one or more indicator lights 22 which provide various operational visual signals, such as malfunction warning signals, for example. Skull covering 14 preferably has sealing material 24 at its skull-contacting periphery so as to prevent stray radiation from escaping. Apparatus 10 preferably includes a timer 26 with an LCD to allow an operator to monitor the irradiation process in real time. Other safety options may be included.

Figure 2:
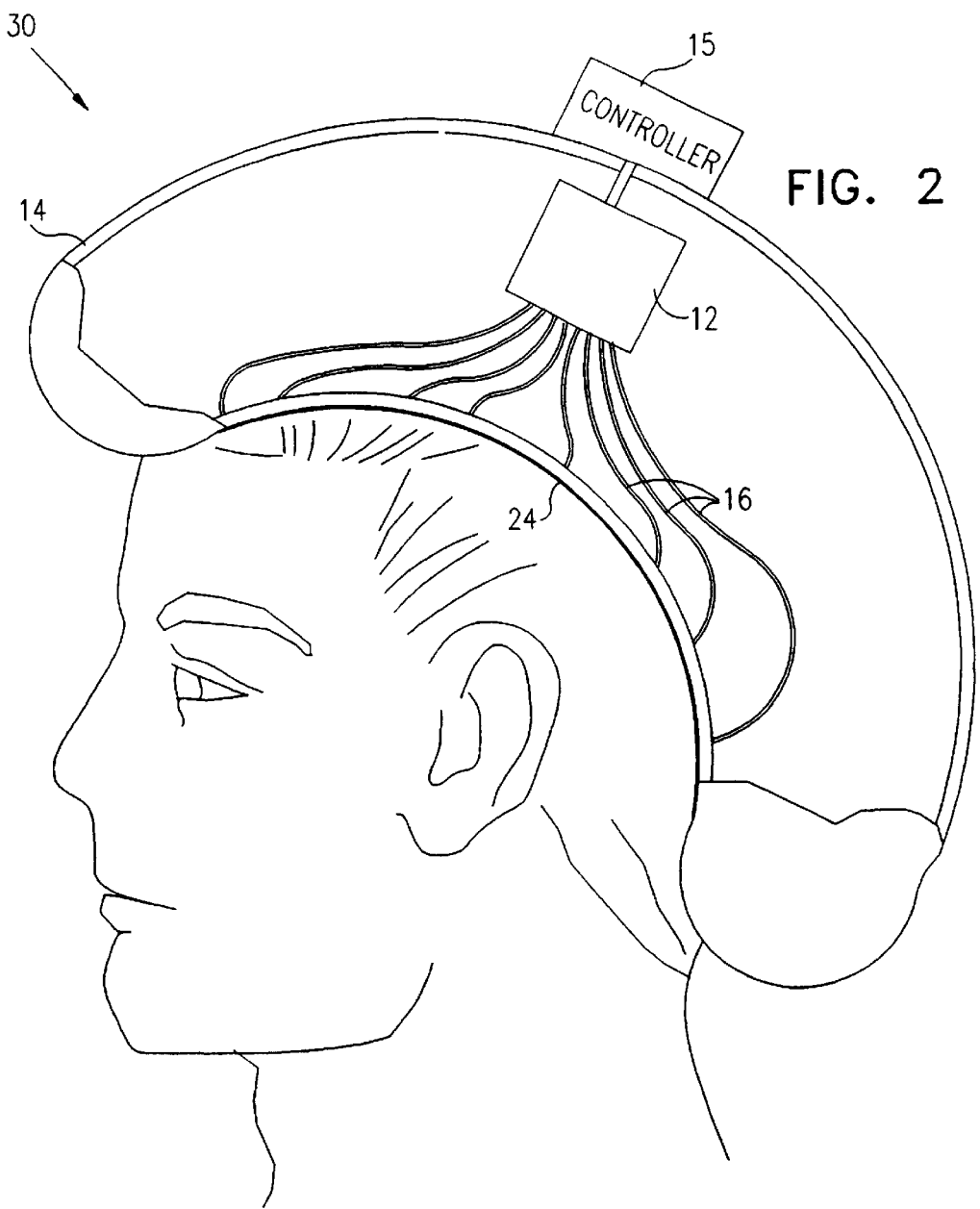
FIG. 2 is a simplified pictorial illustration of apparatus for treatment of an ischemic region of brain cells in a cranium, constructed and operative in accordance with another preferred embodiment of the present invention.

Reference is now made to FIG. 2 which illustrates apparatus 30 for treatment of an ischemic region of brain cells in a cranium, in accordance with another preferred embodiment of the present invention. Apparatus 30 is basically the same as apparatus 10, with like numerals designating like elements, although not all elements are shown in FIG. 2 for the sake of simplicity. Apparatus 30 differs from apparatus 10 in that apparatus 30 includes one laser source 12 and a multiplicity of guides 16 which are arranged for multidirectional multifocal irradiation of the cranium, as described above for apparatus 10.

Figure 3:
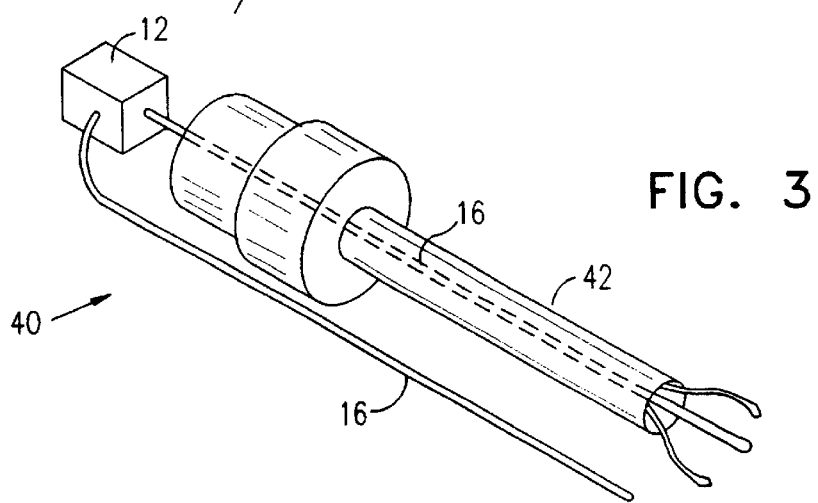
FIG. 3 is a simplified pictorial illustration of apparatus for treatment of an ischemic region of brain cells in a cranium, constructed and operative in accordance with yet another preferred embodiment of the present invention.

Reference is now made to FIG. 3 which illustrates apparatus 40 for treatment of an ischemic region of brain cells in a cranium, in accordance with yet another preferred embodiment of the present invention. Apparatus 40 is basically the same as apparatus 10 or 30, with like numerals designating like elements, although not all elements are shown in FIG. 3 for the sake of simplicity. Apparatus 40 differs from apparatus 10 or 30 in that apparatus 40 also includes a heartbeat sensor probe 42. Guide 16 may be housed inside or outside of probe 42, in accordance with the requirements of the particular application. Apparatus 40 is particularly useful for treating newborn infants, as is now described.

During the process of birth, a newborn may be subject to different kinds of stress-related problems, one example being insufficient oxygen and blood supply to the brain which is a major cause of morbidity and mortality. Factors contributing to brain damage and other adverse outcomes are complex. Both severe hypoxia-ischemia and prolonged hypoxia of lesser severity may cause brain damage (*Low JA*, Cerebral perfusion, metabolism and outcome; *Curr Opin Pediatr*: 7(2): pp. 132–9 Apr 1995). Many morbid conditions are associated with hypoxia such as hypoxic-ischemic encephalopathy, cerebral palsy, microcephaly, seizure disorders, mental retardation, educational failure and others (*Behrman, Kliegman* el al, Nelson's Textbook of Pediatrics, 15$^{th}$ Ed. W. B. Saunders Company: pp.431–3; 1996).

Apparatus 40 is particularly useful for treating newborns, such as during exit from the vagina, wherein laser sources 12 can deliver laser energy to the cranium of the newborn infant quickly and efficiently. In such use for newborns, apparatus 40 may be fashioned without skull covering 14, if desired. Alternatively, an assortment of skull coverings 14 of different sizes and shapes may be provided to a hospital or clinic for perinatal care. Different energy delivery coefficients may be calculated for laser sources 12 depending upon the particular application. The position of the laser sources and the paths of the laser beams into the cranium are based on various factors, such as an anatomical consideration of the newborn (for example, the anatomy of the fontanels).

Apparatus 40 can be combined with conventional monitoring systems and with those under current development. The technique of irradiating the brain with apparatus 40 may be used in conjunction with other methods for protecting the brain, such as the use of glutamate receptor antagonists, glucocorticoids, voltage sensitive calcium channel antagonists etc. (*Tuor UI, Del Bigio MR* el al, Brain damage due to cerebral hypoxia/ischemia in the neonate: pathology and pharmacological modification; *Cerebrovasc Brain Metab Rev,* 8(2): pp 159–93 Summer 1996).

The invention was carried out using the above-described apparatus in two exemplary experiments which are now described.

Experiment I:

The left common carotid artery of 12 mature Sprague-Dawley rats (250–300 gr. body weight anesthetized with Avertin) was exposed by a longitudinal incision to the frontal midline section of the neck. It was then occluded by ligation with a silk (4-0) thread.

The brains of six rats were irradiated by a diode laser. The irradiation was performed by a longitudinal incision in the scalp to expose the skull. The laser source (wavelength 807 millimicron, 400 mW maximal power output) was attached to the parietal bone in the skull (after exposing the skin) at two points: one between the eyes and one 1 cm posterior to the previous one. The duration of each irradiation was 2 minutes. The dispersion of the laser beam after its passage through the skull was measured by an infrared viewer in a preliminary experiment. The energy density that reached the brain tissue was 8 mW per square centimeter. The other six rats had lasers attached to the skull but the lasers were not connected to an energy source Rats were followed up after surgery for various neurological disorders. All the rats that did not receive laser irradiation showed a prolapsed eyelid on the left side and minor motor neurological deficits at 12 hours post occlusion of the left carotid artery.

The six rats that were irradiated as above revealed the following:

One had a prolapsed eyelid on the left side with no other symptoms. all other rats revealed neither eyelid prolapse nor any neurological deficits.

Experiment II:

Occlusion of the left coronary artery was performed on fifteen white mice (25–35 gr.) in a similar method to that described for rats in Experiment I.

Seven of the mice were irradiated with the same laser as in experiment I. The irradiation was performed through the skin that covers the skull. The power output of the laser was set so that the brain of the mice was exposed to an energy of 5 mW/sq. cm. for 2 minutes.

Since the laser beam beyond the skull was dispersed to a diameter of approximately 1.5 cm, only one irradiation in the center of the parietal bone was performed. The irradiation covered the entire dorsal part of the brain.

The other 8 mice served as control animals which went through the same process as the laser irradiated mice, but with the laser not turned on.

After induction of the stroke by ligation of the carotid artery, the mice were observed daily for neurological disorders/ deficits and loss of weight. The results are presented in Table I.

It can be seen from Table I that neurological deficits such as prolapse of the left eyelid and paresis of hind legs (which was also evident by difficulty in locomotion) was significantly higher in the control non-irradiated mice. Furthermore, in 7 out of the 8 non-irradiated mice examined, the ligation of the left carotid artery resulted in up to 50% loss of weight and eventual death. In none of the laser irradiated mice was there a massive weight loss nor did any of them die due to the ligation of the left carotid artery.

It is therefore concluded that laser irradiation most probably has a protective effect on the nerve cells of the CNS or some other protective effect on the CNS as a whole unit. This effect inhibited adverse consequences that usually led to death in this experimental model. It may be postulated that the same protective effect may also be beneficial in the case of stroke or other ischemic events in the CNS of humans.

TABLE I

Effect of Laser Irradiation on mice post ligation of the Left Common Carotid Artery.

| Treatment | Death up to 10 days post ligation. | Paresis in hind legs. | Prolapse of left eyelid. | Significant loss of weight. |
|---|---|---|---|---|
| Control (non irradiated) | 7/8 | 6/8 | 6/8 | 7/8 |
| Laser irradiated | 0/7 | 0/7 | 1/7 | 0/7 |

In addition to the above experiments, penetration of low energy laser irradiation through a human skull was studied using a fresh human skull. A Ga-As diode laser was applied (800 mW maximal output) and a laser meter was placed in the inner side of the skull cavity in order to detect the energy power and dispersion (using a laser infrared viewer) of the laser after penetration through the skull. The beam diameter of the laser was dispersed from 2 mm externally to the skull to 3.5 cm in the skull cavity after penetration through the skull wall in the parietal region of the skull (a width of about 8 mm). The energy density measured inside the skull cavity was 3 mW/sq.cm. In the squamosal region (side region) of the human skull the width of the skull is about 5 mm, so it can be expected that penetration of the laser energy should be better.

The above study shows that the human skull can serve as a "natural lens" that disperses the laser beam so that a larger area of the brain will be laser irradiated. The penetration of low energy laser through the human skull is a feasible option to deliver this energy to the brain cells if the external laser source is operated at the proper power output. This energy will cause a beneficial biostimulation on brain cells after stroke and other related disorders.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. Apparatus for treatment of an ischemic region of brain cells in a cranium, comprising:

a skull covering adapted to cover at least part of a cranium;

at least one guide attached to said skull covering;

a laser source which is operative to direct a laser beam through said at least one guide into a cranium and further comprising an actuator which is operative to vary a region of impingement of said laser beam on said cranium.

2. Apparatus according to claim 1 wherein said at least one guide comprises an optic fiber.

3. Apparatus according to claim 1 wherein said at least one guide comprises a waveguide.

4. Apparatus according to claim 1 wherein said laser source comprises a diode laser.

5. Apparatus according to any of the preceding claims further comprising a laser controller operatively connected to said laser source which controls operation of said laser source.

6. Apparatus according to claim 1 wherein said skull covering comprises sealing material at a skull-contacting periphery thereof.

7. Apparatus according to claim 1 further comprising a timer mounted on said skull covering.

8. Apparatus according to claim 1 further comprising an indicator light mounted on said skull covering.

9. Apparatus according to claim 1 further comprising a plurality of said guides attached to said skull covering which direct a plurality of the laser beams in a plurality of directions.

10. Apparatus according to claim 1 further comprising a plurality of said guides attached to said skull covering which are operative to focus a plurality of the laser beams in a plurality of focal lengths into a cranium.

11. Apparatus according to claim 1 further comprising a plurality of said guides which are commonly attached to said laser source.

12. Apparatus according to claim 1 further comprising a plurality of said laser sources and a plurality of said guides, wherein each source directs a laser beam through one said guide.

* * * * *